(12) United States Patent
Pinel et al.

(10) Patent No.: US 10,942,369 B2
(45) Date of Patent: Mar. 9, 2021

(54) SMART CONTACT LENS CONTROL SYSTEM

(71) Applicant: INTERNATIONAL BUSINESS MACHINES CORPORATION, Armonk, NY (US)

(72) Inventors: Florian Pinel, New York, NY (US); Shikhar Kwatra, Duham, NC (US); Paul Krystek, Highland, NY (US); Sushain Pandit, Austin, TX (US); Sarbajit K. Rakshit, Kolkata (IN)

(73) Assignee: International Business Machines Corporation, Armonk, NY (US)

( * ) Notice: Subject to any disclaimer, the term of this patent is extended or adjusted under 35 U.S.C. 154(b) by 345 days.

(21) Appl. No.: 16/037,972

(22) Filed: Jul. 17, 2018

(65) Prior Publication Data
US 2020/0026097 A1    Jan. 23, 2020

(51) Int. Cl.
| | | |
|---|---|---|
| *G02C 7/04* | (2006.01) | |
| *G05B 13/02* | (2006.01) | |
| *A61B 3/11* | (2006.01) | |
| *A61B 3/14* | (2006.01) | |
| *G06F 3/01* | (2006.01) | |

(Continued)

(52) U.S. Cl.
CPC .............. *G02C 7/04* (2013.01); *A61B 3/11* (2013.01); *A61B 3/14* (2013.01); *G05B 13/0265* (2013.01); *G02C 7/041* (2013.01); *G02C 7/081* (2013.01); *G02C 11/10* (2013.01); *G06F 3/011* (2013.01); *G06F 3/013* (2013.01); *H04N 5/23212* (2013.01); *H04N 5/23219* (2013.01)

(58) Field of Classification Search
CPC .......... G02C 7/04; G02C 7/041; G02C 7/081; G02C 11/10; G06F 3/011; G06F 3/013; G05B 13/0265; H04N 5/23212; H04N 5/23219; A61B 3/113
USPC ............................................. 351/246, 159.03
See application file for complete search history.

(56) References Cited

U.S. PATENT DOCUMENTS 6,478,425 B2 * 11/2002 Trajkovic ............... G02B 7/102
                                                                  351/209
9,671,619 B2    6/2017 Pugh et al.
(Continued)

OTHER PUBLICATIONS

Kaneko, T., "A New, Compact and Quick-Response Dynamic Focusing Lens," Proceedings of International Solid State Sensors and Actuators Conference, Transducers '97, Jun. 19, 1997, pp. 63-66.

(Continued)

*Primary Examiner* — Kristina M Deherrera
(74) *Attorney, Agent, or Firm* — Conley Rose, P.C.

(57) ABSTRACT

A computer program product comprising a computer readable storage medium having program instructions embodied therewith, the program instructions executable by a processor of a smart contact lens. Executing the instructions causes the smart contact lens to measure dimensions of a user's eye to determine a focal length of the user, measure a magnetic field proximate to the user's eye to determine a direction of focus of the user, receive a control input from the user, determine a control signal corresponding to the focal length of the user, the direction of focus of the user, and the received control input, generate the determined control signal, and control a first electronic device by transmitting, by the smart contact lens, the generated control signal to the first electronic device.

20 Claims, 7 Drawing Sheets

(51) Int. Cl.
*H04N 5/232* (2006.01)
*G02C 11/00* (2006.01)
*G02C 7/08* (2006.01)

(56) References Cited

U.S. PATENT DOCUMENTS

| | | |
|---|---|---|
| 9,843,385 B2 | 12/2017 | Deyle et al. |
| 2012/0242698 A1* | 9/2012 | Haddick ............ G02B 27/0176 345/633 |
| 2013/0169530 A1 | 7/2013 | Bhaskar et al. |
| 2014/0081178 A1* | 3/2014 | Pletcher ................. A61B 3/113 600/595 |
| 2014/0098226 A1 | 4/2014 | Pletcher et al. |
| 2015/0362756 A1 | 12/2015 | Wiser et al. |
| 2016/0270656 A1* | 9/2016 | Samec ................. A61B 3/1216 |
| 2016/0342782 A1 | 11/2016 | Mullins et al. |
| 2017/0270636 A1 | 9/2017 | Shtukater |
| 2017/0371184 A1 | 12/2017 | Shtukater |

OTHER PUBLICATIONS

Creighton, J., "Bionic Contacts; Goodbye Glasses. Hello Vision That's 3x Better Than 20/20," Hard Science, May 23, 2015, 4 pages.
Wikipedia, "Eye tracking," Jul. 9, 2018, 13 pages.
Dahlberg, J., "Eye Tracking With Eye Glasses," Jan. 25, 2010, 66 pages.
Anthony, S., "Google invents smart contact lens with built-in camera: Superhuman Terminator-like vision here we come," Apr. 15, 2014, 5 pages.
"Google Lens: Everything you need to know," Oct. 6, 2017, 3 pages.
Crider, M., "Google Patent Application Shows Multi-Sensor Contact Lenses for Wareable Device Input Via Blinks," Mar. 22, 2014, 2 pages.
Woodford, C., "Compasses," Jul. 7, 2017, 9 pages.
Wikipedia, "Lens (Anatomy)," Jul. 9, 2018, 9 pages.
Whitney, L., "Samsung's 'eye mouse' enables users to control their computer with a glance," Nov. 25, 2014, 2 pages.
Edwards, L., "Smart contact lenses: What's the story so far'?," May 5, 2016, 7 pages.
Miller, S., "Smartphone-Connected Contact Lenses Give New Meaning to 'Eye Phone'," Aug. 19, 2016, 2 pages.
"Sony Patents Contact Lens Cam with Zoom, Aperture Control, and More," Apr. 28, 2016, 2 pages.
"Understanding Camera Lenses," http://curta.dlinkddns.com/html_photography/Understanding_camera_lenses/understanding_Camera_lenses.htm, 7 pages.
WebGazer.js, "Democratizing Webcam Eye Tracking on the Browser," 2018, 10 pages.
Elgan, M., "Why a smart contact lens is the ultimate wearable," May 9, 2016, 5 pages.

* cited by examiner

SMART CONTACT LENS CONTROL SYSTEM

BACKGROUND

The present disclosure relates to the field of cognitive computing, and more specifically to control of objects utilizing cognitive processing of smart lens input.

Through advancements and minimization of technology, it has become possible to incorporate electronic components and circuits into devices previously impossible. With the incorporation of electronic components into these newly possible devices, new possibilities for incorporation into the daily lives of users becomes possible and leads to the potential for new control methods and/or improved control methods for other existing devices that would be controlled in other ways prior to existence of the newly possible devices.

SUMMARY

Aspects of the present disclosure provides for a computer program product comprising a computer readable storage medium having program instructions embodied therewith. The program instructions are executable by a processor of a smart contact lens to cause the processor of the smart contact lens to measure, by the smart contact lens, dimensions of a user's eye to determine a focal length of the user, measure, by the smart contact lens, a magnetic field proximate to the user's eye to determine a direction of focus of the user, receive, by the smart contact lens, a control input from the user, determine, by the smart contact lens, a control signal corresponding to the focal length of the user, the direction of focus of the user, and the received control input, generate, by the smart contact lens, the determined control signal, and control a first electronic device by transmitting, by the smart contact lens, the generated control signal to the first electronic device.

Other aspects of the present disclosure provide for a computer-implemented method. The computer-implemented method comprises measuring, by a smart contact lens, dimensions of a user's eye to determine a focal length of the user, measuring, by the smart contact lens, a magnetic field proximate to the user's eye to determine a direction of focus of the user, receiving, by the smart contact lens, a control input from the user, determining, by the smart contact lens, a control signal corresponding to the focal length of the user, the direction of focus of the user, and the received control input, generating, by the smart contact lens, the determined control signal, and controlling a first electronic device by transmitting, by the smart contact lens, the generated control signal to the first electronic device.

Other aspects of the present disclosure provide for a system comprising a smart contact lens and a processing device. The smart contact lens is configured to determine an object on which a wearer of the smart contact lens is focusing, determine a control input provided by the wearer of the smart contact lens, generate a first control signal for controlling a first electronic device according to a result of a machine learning process including the determining of the object on which the wearer of the smart contact lens is focusing and the control input provided by the wearer of the smart contact lens. The processing device is configured to receive a plurality of signals from the smart contact lens, based on the received plurality of signals, determine an association between the object on which a wearer of the smart contact lens is focusing, the control input provided by the wearer of the smart contact lens, and the first control signal, and provide the association between the object on which a wearer of the smart contact lens is focusing, the control input provided by the wearer of the smart contact lens, and the first control signal.

DETAILED DESCRIPTION

Figure 1:
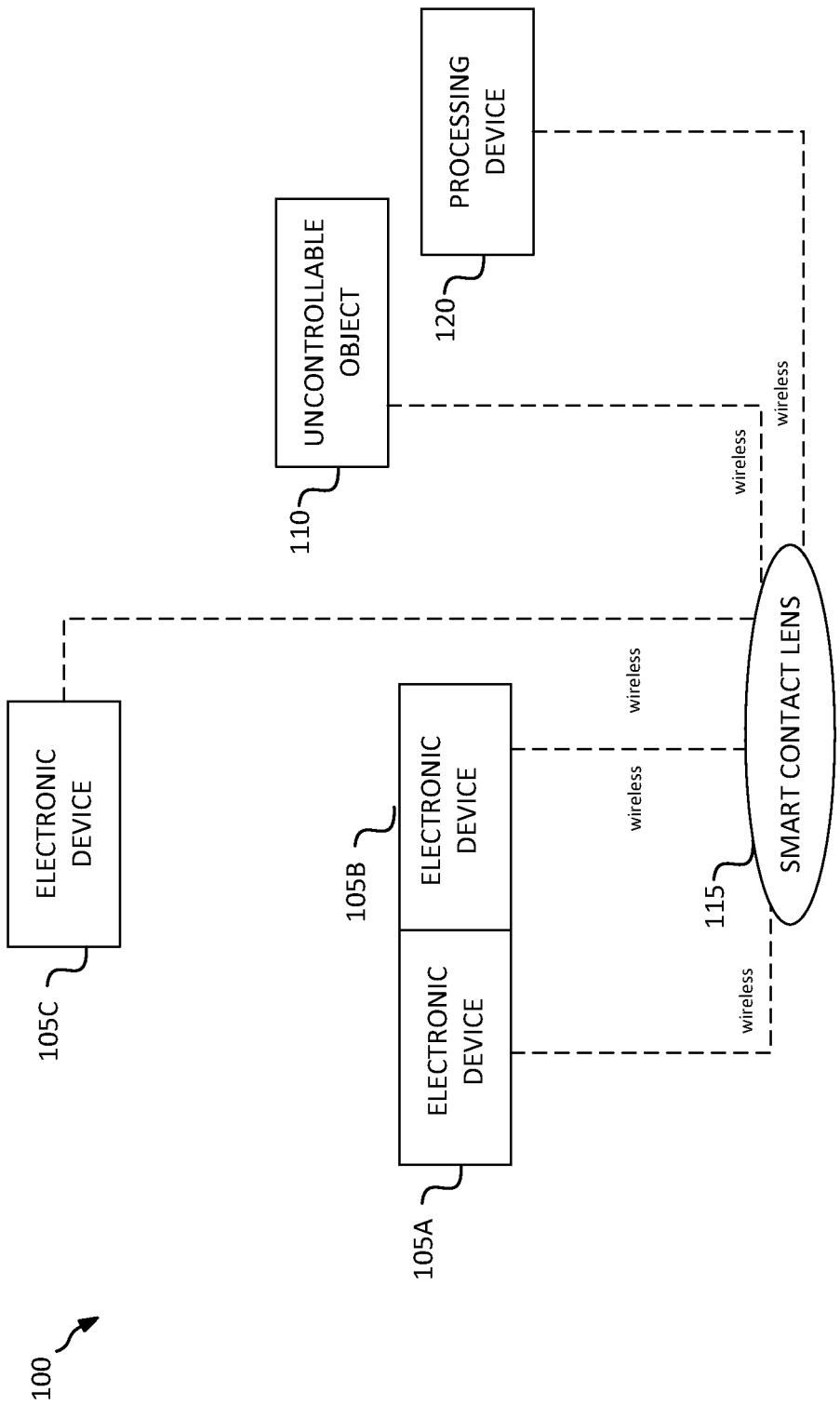
FIG. 1 is a block diagram of an illustrative smart contact lens control system in accordance with various embodiments.

Electronic component miniaturization has enabled the inclusion of electronic components in the periphery of contact lenses. For example, some electronic components are suitable for inclusion in a contact lens outside of a field of view of a wearer of the contact lens (referred to herein as a user), such as in an area of the contact lens overlapping the sclera of the user's eye. In other examples, at least some of the electronic components at least partially overlap the cornea (or corneal lens) of the user's eye. Integrating electronic components in a contact lens, in some examples, create opportunities for using the electronic components as an interface for the user to interact with or control other electronic devices nearby. However, challenges may arise in implementing such control, for example, in distinguishing which particular electronic device a user wishes to control when looking at an area or in a direction of multiple electronic devices (e.g., multiple electronic devices stacked vertically or arranged horizontally). Challenges may also arise in implementing control when multiple electronic devices are in a single line of sight of the user but located at a plurality of distances from the user. Challenges may further arise in implementing control of at least one of the electronic devices using a touchless control interface (e.g., an optical control interface) without using hand-based gestures to perform the control.

Disclosed herein are embodiments that provide for a smart contact lens that enables control of one or more electronic devices based on inputs received and/or determined by the smart contact lens. For example, at least some of the disclosed embodiments provide for a smart contact lens that functions as an interface between the user and the environment around the user (e.g., physical or virtual environment observable by the user). Some examples of the smart contact lens include a backside-facing camera facing toward the user's retina. Some examples of the smart contact lens also, or alternatively, include a magnetic sensor. Yet other examples of the smart contact lens also, or alternatively, include an accelerometer (e.g., a nano-accelerometer) and various supporting electronic components (e.g., transmitters, receivers, processors, power harvesting and/or storage elements, etc.), the scope of which is not limited herein. In an operational example of the smart contact lens, when the smart contact lens is in use the backside-facing camera scans the retina to identify and authenticate the user. Based on movements of the user's head and/or eyes, a magnetic field proximate to the smart contact lens will change and the magnetic sensor will detect the change in the magnetic field. Additionally, in some examples the accelerometer further detects movement of the user's head and/or eyes and, in yet other examples, the backside-facing camera further determines a shape of the user's eye. Each determined measurement or signal is transmitted by the smart contact lens to a processing device for processing the measurements or signals, generating a control signal for controlling the electronic devices, and transmitting the control signal. In various examples, the smart contact lens, the processing device, or both, perform validation of the control signal via additional inputs received from the user (e.g., inputs provided by the user to the processing device and/or via the smart contact lens). For example, the user may make one or more movements of the user's head to provide positive or negative feedback in response to the control signal (e.g., indicate that the control signal performed the desired action or did not perform the desired action). The user feedback is used, in at least some examples, in a machine-learning process of the processing device and/or the smart contact lens to improve generation of control signals based on inputs received from the smart contact lens.

Referring now to FIG. 1, a block diagram of an illustrative smart contact lens control system 100 in accordance with various embodiments is shown. The system 100, in at least some examples, is implemented to perform control of one or more electronic devices based on input signals detected by the smart contact lens. In one example, the system 100 includes a plurality of electronic devices 105A, 105B, and 105C (105A-105C) and an uncontrollable object 110. While four electronic devices are shown in FIG. 1 for illustrative purposes, a number of electronic devices in the system 100 is not limited herein. The system 100 further includes a smart contact lens 115 and a processing device 120. In various examples, although not shown, the system 100 also includes one or more devices for facilitating wireless communication among the devices of the system 100 and/or between one or more devices of the system 100 and one or more other devices outside of the system 100 such as cloud computing devices or other Internet-connected devices.

The electronic devices 105A-105C are any electronically controllable devices, the scope of which is not limited herein. For example, any one or more of the electronic devices 105A-105C are be controllable via infrared (IR) signals, radio frequency (RF) signals, near-field communication (NFC) signals, and/or any other communication protocol suitable for conveying information to, or FROM, the electronic devices 105A-105C. The uncontrollable object 110 is any object lacking the ability to be controlled via receipt of one or more electronic signals. For example, the uncontrollable object 110 may be a tree, a sign, a lamppost, a chair, a clock, a doorknob, or any other object lacking the ability to be electronically controlled.

Figure 2:
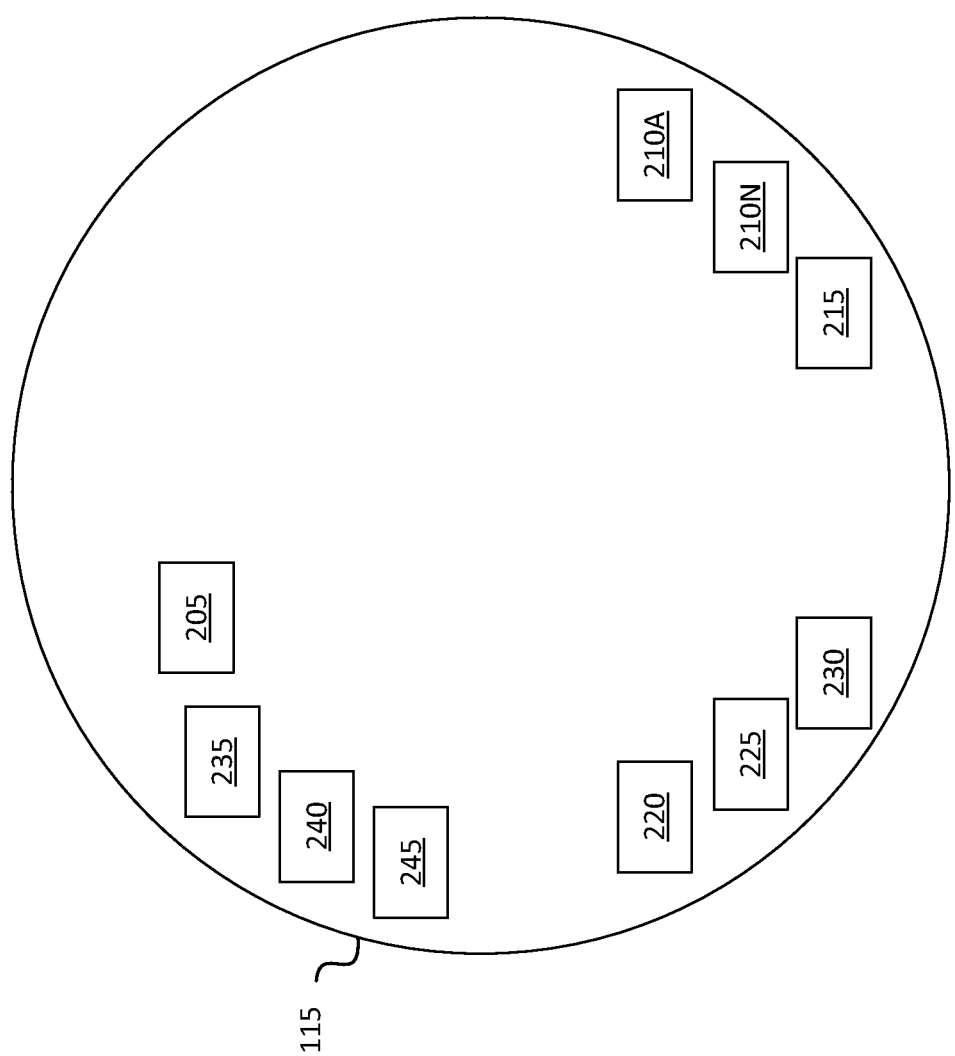
FIG. 2 is a block diagram of an illustrative smart contact lens in accordance with various embodiments.

The smart contact lens 115 is a device configured to interface with the user's eye. In some examples, the smart contact lens 115 is configured to be implanted into the user's eye or configured to lie beneath the user's eyelids and on top of the user's cornea. The smart contact lens 115 includes a plurality of electrical components, the scope of which is not limited herein. For example, the smart contact lens 115 includes a backside facing camera (e.g., an IR camera pointed into the user's eye), an outward facing camera pointed away from the user's eye, a power system, a magnetic sensor, an accelerometer, a receiver, one or more transmitters (e.g., NFC, IR, RF, etc.), a processor, a memory, and/or any other electrical components suitable for performing the operations disclosed herein. In some examples, the smart contact lens 115 includes non-electronic optical enhancement (e.g., eyesight power correction) built-in or inherent to the construction of the smart contact lens 115. In other examples, the smart contact lens 115 includes electronic optical enhancement (e.g., magnification). In some examples, the smart contact lens 115 includes circuitry or other electrical components for displaying one or more digital images on a surface of the smart contact lens 115 and/or projecting a digital image into a space outside of the smart contact lens 115 (e.g., appearing in front of the user, to the sides of the user, etc.). One exemplary smart contact lens 115 is illustrated in FIG. 2 and includes a backside facing camera 205 (e.g., an IR camera), one or more front-side facing cameras 210A . . . 210N, a magnetic sensor 215, an accelerometer 220, a processor 225, data storage 230, and transceiver 235 (which, in some examples, is generally representative or takes the form of one or more transmitters or receivers). In some examples, the exemplary smart contact lens 115 further includes other sensors 240 such as pressure sensors, temperature sensors, or the like, and a power system 245. In various examples, any one or more of the backside facing camera 205, front-side facing cameras 210A . . . 210N, magnetic sensor 215, accelerometer 220, and/or sensors 240 perform measurements or otherwise capture data that is processed by the processor 225 and/or transmitted by the transceiver 235. In other examples, the captured data is stored in the data storage 230 before, after, or both before and after processing by the processor 225. In some examples, the transceiver 235 receives one or more signals for processing by the processor 225 and/or storage in the data storage 230. The power system 245 is configured to provide power for operation of each component of the smart contact lens 115.

Returning now to FIG. 1, the processing device 120 is any device capable of receiving signals from the smart contact lens 115, transmitting signals to the smart contact lens 115, transmitting signals to one or more of the electronic devices 105A-105C, and/or processing data received from the smart contact lens 115. In some examples, the processing device 120 is a smart phone. In other examples, the processing device 120 is a laptop computer, a desktop computer, a server, a cloud computing node, or any other device suitable for performing the processing and operations of the present disclosure.

In an example of operation of the system 100, the smart contact lens 115 controls one or more of the electronic devices 105A-105C based on control inputs received from the user. In various examples, the control inputs take numerous forms, the scope of which is not limited herein. For example, the control inputs include detections, determinations, and/or measurements of any one or more control gestures such as a prolonged gaze at one of the electronic devices 105A-105C or the uncontrollable object 110 (e.g., a period of intense visual focus on one of the electronic devices 105A-105C or the uncontrollable object 110), movement of the user's eyes, movement of the user's eyelids, movement of the user's head, movement of the user's body, gestures made by the user's hands in view of the user's eyes (and therefore the smart contact lens 115), or any combination of the foregoing.

In some examples, the user controls one or more of the electronic devices 105A-105C based on controls inputs received by the smart contact lens 115 while the user views the one or more of the electronic devices 105A-105C being controlled. For example, when the user focuses on one of the electronic devices 105A-105C and performs one of the control gestures, the electronic devices 105A-105C, a control signal is transmitted to the one of the electronic devices 105A-105C focused on by the user. In some examples, the smart contact lens 115 determines and transmits the control signal. In other examples, the processing device 120 determines and transmits the control signal, for example, based on one or more signals received by the processing device 120 from the smart contact lens 115 and including at least some of the control inputs. In various examples, the control signal is transmitted substantially directly from the smart contact lens 115 or the processing device 120 to one or more of the electronic devices 105A-105C, via a plurality of nodes (e.g., such as mesh network nodes or Internet-of-Things (IOT) nodes), or via the Internet and one or more networking devices facilitating Internet-based communication.

In other examples, the user controls one or more of the electronic devices 105A-105C based on controls inputs received by the smart contact lens 115 while the user views the uncontrolled device 110. For example, when the user focuses on the uncontrollable object 110 and performs one of the control gestures, the smart contact lens 115 transmits a control signal to one or more of the electronic devices 105A-105C and/or to the processing device 120. For example, the uncontrollable object 110 represents a virtual icon that, based on one of the control gestures, triggers control of one or more of the electronic devices 105A-105C and/or to the processing device 120. In some examples, the user indicates a correspondence between the virtual icon, a particular control gesture, and a particular control signal or action for the one or more of the electronic devices 105A-105C and/or to the processing device 120, such as during a training operation of the system 100. In some examples, the user defines a scene (e.g., a group of actions to be performed together or in a particular order) when the user performs the particular control gesture while focusing on the virtual icon.

In yet other examples, the user controls one or more virtual elements based on controls inputs received by the smart contact lens 115 while the user views the virtual elements. For example, the smart contact lens is suitable for use in a virtual reality environment or an augmented reality environment in which virtual elements are presented to the user (e.g., via the smart contact lens 115 and/or via any other device) and the user interacts with the virtual elements via one or more of the control gestures. In various examples, the user interacts with the virtual elements by the smart contact lens 115 modifying one or more of the virtual elements, or a visual presentation of the one or more of the visual elements, based on the control inputs received by the smart contact lens 115. In another example, the user interacts with the virtual elements by the processing element 120 modifying one or more of the virtual elements, or a visual presentation of the one or more of the visual elements, based on control inputs received from the smart contact lens 115.

When a user focuses on an object, whether it is one of the electronic devices 105A-105C or the uncontrollable object 110, characteristics of, and around, the user's eye will change. For example, as the user's eyes shift upward, downward, to either side, or the user's head moves, a magnetic field in an area immediately around the smart contact lens 115 will change. Similarly, as the user focuses on the object, a shape of the user's eye will subtly change based on a distance of the object from the user's eye (e.g., the focal length). By measuring these two characteristics, the smart contact lens 115 determines the object on which the user is focusing. When the user performs a control gesture while focusing on the object, the smart contact lens 115 generates and transmits a control signal to one of the electronic devices 105A-105C based on the object that the user is focusing on, the control gesture, and an association among the object that the user is focusing on, the control gesture, and a predefined action specified by the user during training or customization (e.g., preference specification) of the system 100. In some examples, the smart contact lens 115 measures the magnetic field using a magnetic sensor and measure the shape of the eye using a backside IR camera. In other examples, the magnetic field measurement and determination of the shape of the user's eye are further supplemented by input received by the smart contact lens 115 from an accelerometer, a front-side facing camera that generally views what the user is viewing, a pressure sensor, a temperature sensor, or the like.

The smart contact lens 115 utilizes any number of control inputs in determining the object that the user is focusing on and/or the control gesture, the scope of which is not limited herein. In some examples, when the object is very near to the user, the smart contact lens 115 uses fewer control inputs in determining the object that the user is focusing on and/or the control gesture. In other examples, when the object is far from the user, the smart contact lens 115 uses a greater number of control inputs in determining the object that the user is focusing on and/or the control gesture. In at least some examples, the smart contact lens 115 includes no distance limitations other than a distance of sight of the user for control of, or determining, the object on which the user is focusing. For example, if the user can see the object, regardless of distance from the user, the smart contact lens 115 is capable of generating a control signal to control at least one of the electronic devices 105A-105C. In at least some examples, the system 100 is further operable when the user utilizes visual assistance or enhancement devices such as binoculars (e.g., analog or digital), or when the user focuses on a visual image of the object (e.g., a photograph of the object). In an example in which the user can see the object, regardless of distance from the user, the smart contact lens 115 attempts to transmit the generated control signal according to one or more near field communication protocols. In an example in which the user focuses on a visual image of the object, or the smart contact lens 115 is unable to transmit the generated control signal according to the one or more near field communication protocols, the smart contact lens 115 attempts to transmit the generated control signal using one or more other communication protocols such as cellular communication protocols, wireless networking, a Wide Area Network, a Cloud Computing environment, or any other communication protocol that is not a near field communication protocol. In some examples, the user provides one or more preferences (via interaction and/or training, as discussed herein, with the processing element 120 and/or the smart contact lens 115) to limit the ability to generate control signals based on focusing on the object or the visual image of the object. For example, in some implementations the ability of the smart contact lens 115 to generate the control signal is limited based on a geospatial position of the user (e.g., as determined by the smart lens 115 and/or the processing element 120) such that the smart contact lens only generates the control signal based on focusing on the object or the visual image of the object when the user is within a predefined or specified geospatial area. The ability of the system 100 to implement control of devices far from the user, in at least some examples, improves over other smart systems that provide control only for nearby devices where the device being controlled monitors (e.g., via line of sight and/or particular positioning of the user in relation to the device being controlled) the user for control input and executes the control based on the inputs and/or requires handheld or hand-based actions for providing the control input and/or performing the control.

In at least some examples, each time one or more of the electronic devices 105A-105C takes action based on a control signal generated by, or according to control inputs measured by, the smart contact lens 115, one or more signals are transmitted by the smart contact lens 115 to the processing device 120. The signals include, for example one or more measurements made by the smart contact lent 115 of the control inputs (e.g., accelerometer output and/or magnetic sensor output), a signal strength of a wireless coupling between the smart contact lens 115 and the one of the electronic devices 105A-105C, and feedback provided by the user. The feedback is be provided in any suitable manner, including at least the control gestures and control input discussed above. The feedback, in at least some examples, indicates whether the smart contact lens 115 accurately determined the object that the user was focusing on, correctly determined the control inputs and/or the control gesture, and/or determined the correct control signal corresponding to the object that the user was focusing on and the control inputs and/or the control gesture. The feedback is be utilized, in some examples, in an ongoing refinement process by the smart contact lens 115 and/or the processing device 120 to refine the association among objects that the user focuses on, control inputs, control gestures, and corresponding action for one or more of the electronic devices 105A-105C. In some examples, the feedback is utilized in a machine-learning process for generating and/or refining associations among objects that the user focuses on, control inputs, control gestures, and corresponding action for one or more of the electronic devices 105A-105C.

The smart contact lens 115, in some examples, is operable in a training mode that trains the smart contact lens 115 and/or the processing device 120 to recognize the control inputs, control gestures, and/or develop associations among objects that the user focuses on, control inputs, control gestures, and corresponding action for one or more of the electronic devices 105A-105C. The training mode is at least partially implemented according to a machine-learning process. In some examples, the user utilizes and/or invokes a user interface of the processing device 120 to enter the training mode. In some examples, the user focuses on one or more of the electronic devices 105A-105C and/or the uncontrollable object 110 such that the processing device 120 learns an image of the objects focused on by the user and a relation of measurements made by the smart contact lens 115 to the devices. In one example, the user is positioned in a customary location for focusing on one of the objects (e.g., sitting on a couch and focusing on a television located near the couch) and the processing device 120 learns a size and/or shape of the user's eye corresponding to focusing on that particular object from the customary position of the user based on measurements taken by the smart contact lens 115. In some examples, the processing device 120 further learns the appearance of particular gestures of the user intended to be control gestures and/or control inputs of the user that are intended to correspond to generation of a control signal as opposed to a purpose tangential to operation of the system 100.

For example, the user may be looking into the distance in thought followed by the user's eyes looking to one side or the other. In some examples, the focal point of the user's view is on, or near, one of the electronic devices 105A-105C and/or the uncontrollable object 110 and a quick diversion of the user's eyes to the side corresponds to a control input for controlling one of the electronic devices 105A-105C. However, in the above context of the user in thought, the user may not wish to control one of the electronic devices 105A-105C at that time. In some examples, the training mode, and particularly a machine learning processing of the training mode, enables the processing device 120 to distinguish a difference between the user's look to the side and a quick diversion of the user's eyes to the side, as well as an amount of time of the user's focus on the object prior to, or after, the control input is measured. Based on this learning by the processing device 120, the processing device 120 generates and/or modifies correspondences associated with generating control signals such that the smart contact lens 115 is taught which control inputs and/or control gestures correspond to desired control signals and which control inputs and/or control gestures are tangential to the system 100 and should not result in generation of a control signal. In some examples, the learning of the processing device 120 is refined based on user feedback, as discussed above, each time one of the electronic devices 105A-105C performs a function responsive to receipt of a control signal.

While the discussions of the present disclosure illustrate the processing device 120 as performing the machine learning processing to teach the smart contact lens 115, in at least some examples, some portion of the processing discussed with reference to the processing device 120 is performed by the smart contact lens 115. In other examples, all of the processing discussed with reference to the processing device 120 is performed by the smart contact lens 115 such that the processing device 120 may be omitted from the system 100 without affecting functionality of the system 100. In some examples, the smart contact lens 115 is an all-in-one device that performs the machine learning, stores the resulting data, captures data, processes the captured data, determines an action, if any, corresponding to the captured data, generates and transmits a control signal, and, optionally, receives one or more signals in reply.

Figure 3:
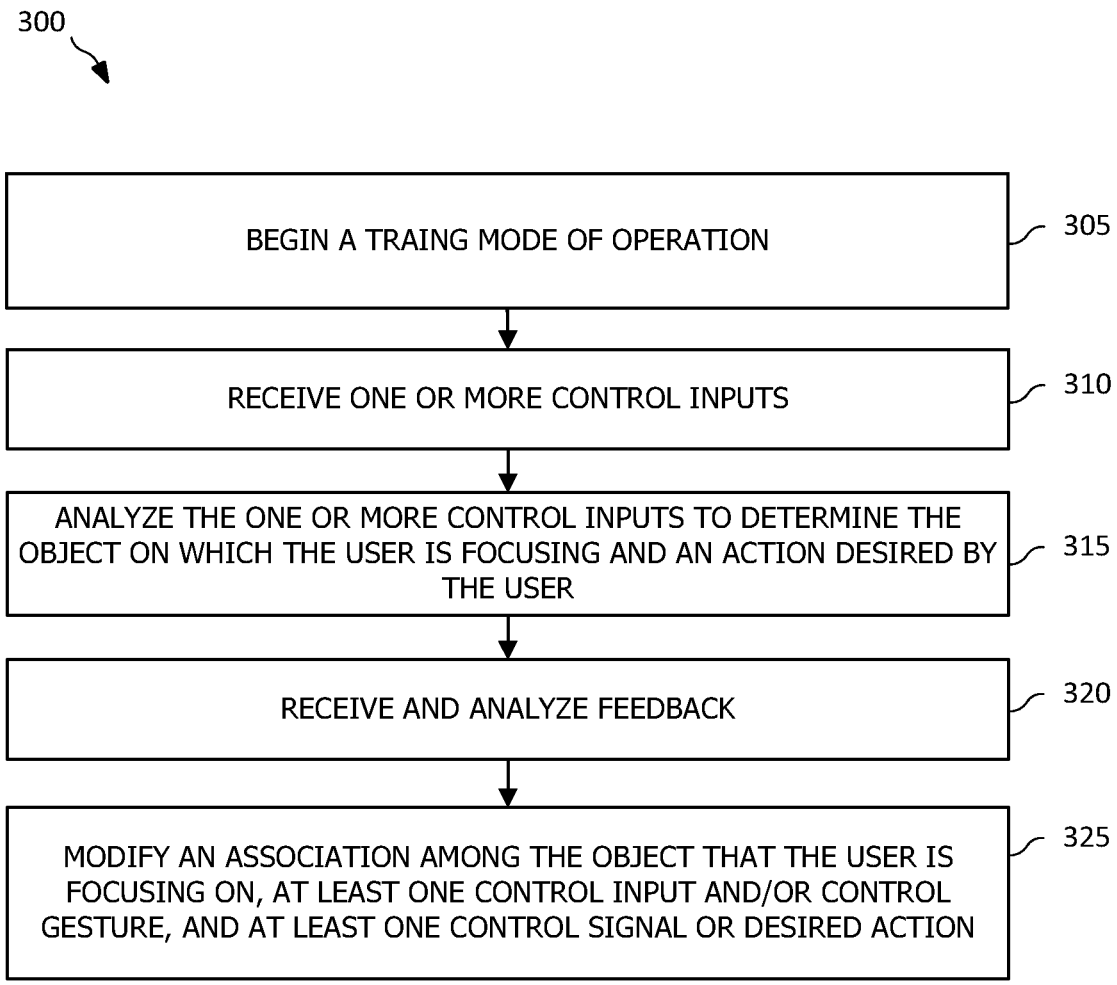
FIG. 3 is a flowchart of an illustrative method of smart contact lens training in accordance with various embodiments.

Turning now to FIG. 3, a flowchart of an illustrative method 300 of smart contact lens training in accordance with various embodiments is shown. The method 300 is implemented, in some examples, to train the smart contact lens 115 and/or the processing device 120 to control one or more of the electronic devices 105A-105C based on an object on which the user focuses, one or more control inputs, and one or more control gestures. In at least some examples, the method 300 is implemented by one or more components of the system 100. For example, the method 300 is suitable for implementation at least partially by the smart contact lens 115 and at least partially by the processing device 120. In other examples, the method 300 is suitable for implementation by the smart contact lens 115 without the use of the processing device 120.

At operation 305, a training mode of operation begins. The training mode of operation, in some examples, includes repeatedly performing the same control input or control gesture while located at one or more distances from an object on which the user is focusing. In some examples, the training mode further includes the user accessing a user interface of a training program and providing one or more preferences, such as preferred control inputs and/or preferred gestures to correspond to one or more of the electronic devices 105A-105C or the uncontrollable object 110 and/or a control signal (e.g., to cause a desired action).

At operation 310, one or more control inputs are received. The control inputs are, for example, measurements made by the smart contact lens and can include an output of a magnetic sensor, an output of an accelerometer, output of one or more cameras, and/or output of any other suitable sensors. In one example, at least one of the inputs is a measurement of a magnetic field proximate to the smart contact lens and a second of the inputs is a measurement of the shape and/or size of the user's eye. In another example, the inputs also include image data captured by a front-facing camera or imaging sensor and/or measurements of motion of the user's eyes or head. In at least some other examples, the control inputs include data corresponding to one or more control gestures. The control gestures can include eye movement, head movement, body movement, gestures, or any combination(s) thereof.

At operation 315, the control inputs are analyzed to determine the object on which the user is focusing and an action desired by the user. In various examples, the desired action is of an object other than the object on which the user is focusing (e.g., when the user is focusing on a virtual icon, as discussed above) or the desired action is of the object that on which the user is focusing. Optionally, operation 315 further includes the user interacting with one or more user interfaces (e.g., presented by the smart contact lens 115 and/or the processing device 120) to indicate explicit user preferences. In some examples, the user creates a correspondence between certain objects, control gestures, and control signals (e.g., to generate scenes). In other examples, the user also creates a correspondence between a particular control input or control gesture and a control signal based on the object on which the user is focusing and/or a general class to which the object on which the user is focusing belongs.

At operation 320, feedback is received and analyzed. The feedback is, for example, user input indicating whether a control signal corresponding to the object on which the user is focusing, a control input, and/or a control gesture performed a function that the user intended or desired. The feedback is be provided though an additional control input or control gesture and/or via input by the user through a user interface of the smart contact lens 115 and/or the processing device 120. Optionally, other data is received and analyzed separately from, or along with, the feedback. In some examples, the other data indicates a signal strength of a communication channel between the smart contact lens 115 and at least one of the one or more electronic devices 105A-105C that received a control signal and/or other control input data captured by the smart contact lens 115 (e.g., accelerometer output data).

At operation 325, the association among the object that the user is focusing on, at least one control input and/or control gesture, and at least one control signal or desired action is modified based on the analysis of operation 320. For example, when the analysis performed at operation 320 reveals that the user regularly provides negative feedback for a particular association among the object that the user is focusing on, at least one control input and/or control gesture, and at least one control signal or desired action, the association is modified based on that negative feedback. For example, a modification is made such that the control signal is no longer generated for that particular association among the object that the user is focusing on, at least one control input and/or control gesture, and at least one control signal or desired action. As an example, a threshold value for generating the control signals is modified such that the generation of the control signal requires a more exaggerated action to provide the control input and/or control gesture, performance of the control input and/or the control gesture for a greater period of time, etc. In various examples, the method 300, and particularly operations 320 and 325, is implemented in an ongoing manner such that the associations among objects that the user is focusing on, control inputs and/or control gestures, and control signals or desired actions are continually refined and modified according to feedback provided by the user, usage habits of the user (e.g., which actions of the user correspond to intended control inputs and/or control gestures and which similar actions are not intended to correspond to intended control inputs and/or control gestures), movement or change in the electronic devices 105A-105C and/or the uncontrollable object, changes in characteristics of the user's eyes (e.g., change in shape or size as the user ages, change in a baseline magnetic field present proximate to the user's eye, etc.), and/or other suitable criteria.

Figure 4:
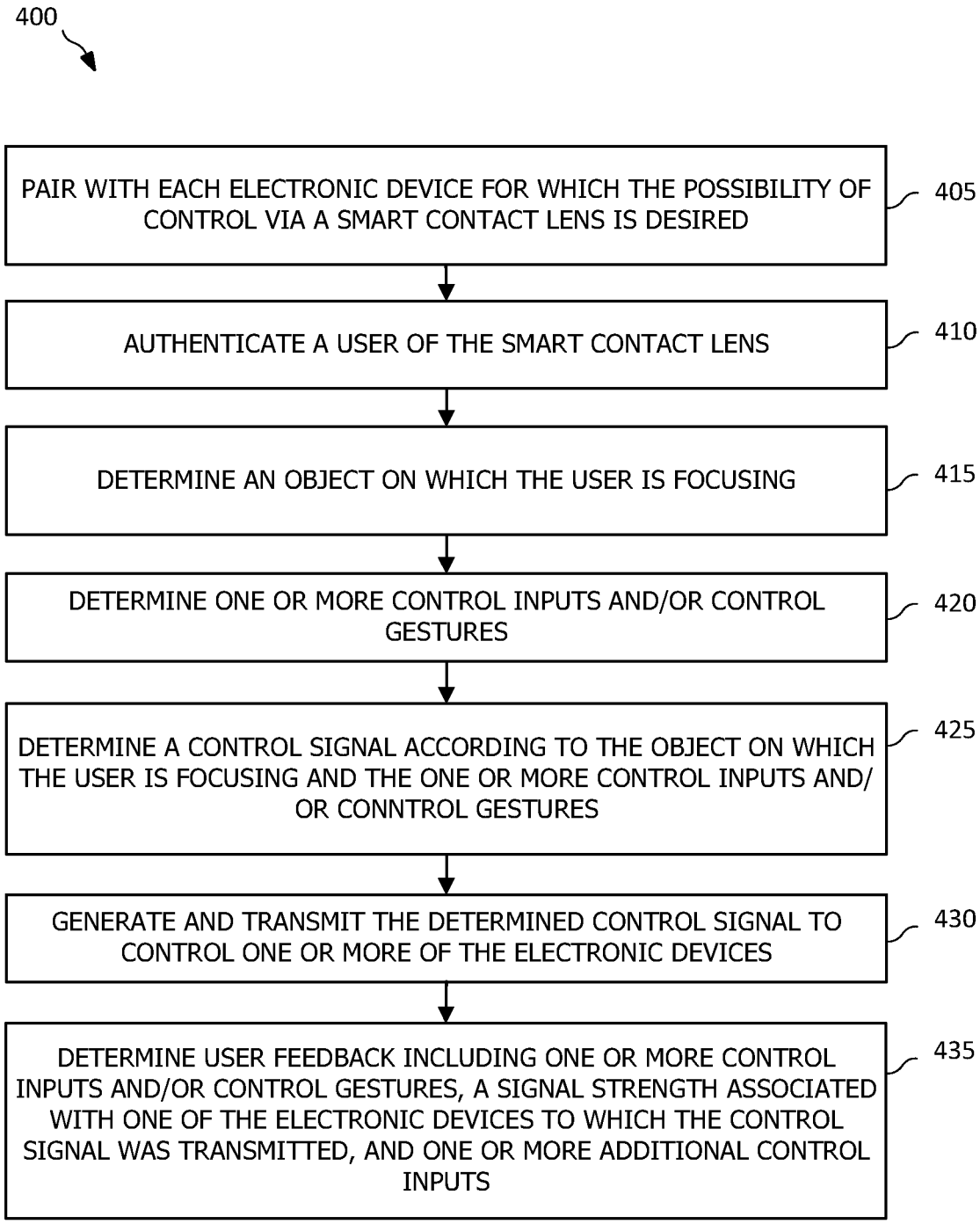
FIG. 4 is a flowchart of an illustrative method of smart contact lens control in accordance with various embodiments.

Turning now to FIG. 4, a flowchart of an illustrative method 400 of smart contact lens control in accordance with various embodiments is shown. The method 400 is implemented, in some examples, to control one or more of the electronic devices 105A-105C based on an object on which the user focuses, one or more control inputs, and/or one or more control gestures. In at least some examples, the method 400 is implemented by one or more components of the system 100. For example, the method 400 is suitable for implementation implemented at least partially by the smart contact lens 115 and at least partially by the processing device 120. In other examples, the method 400 is suitable for implementation by the smart contact lens 115 without the use of the processing device 120.

At operation 405, the smart contact lens 115 pairs with each of the electronic devices 105A-105C for which the possibility of control via the smart contact lens 115 is desired. The pairing process can take various forms according to a particular communication protocol utilized between the smart contact lens 115 pairs and each of the electronic devices 105A-105C, and a scope of this pairing process is not limited herein. In at least one example, the pairing process include the smart contact lens 115 exchanging identifying information with each of the each of the electronic devices 105A-105C and/or authentication or authorization information to enable the electronic devices 105A-105C to identify a control signal received from the smart contact lens 115 as being an authentic control signal.

At operation 410, the smart contact lens 115 authenticates the user. In some examples, the smart contact lens 115 authenticates the user by scanning the user's eye. The scanning is performed, for example, by a camera (e.g., an IR camera) of the smart contact lens 115 scanning the retina of the user's eye. In some examples, the smart contact lens 115 compares data from the scanned retina of the user to an internally stored control data indicating an authenticated user. In other examples, the smart contact lens 115 transmits the data from the scanned retina of the user to the processing device 120 for the processing device to determine whether the data from the scanned retina of the user matches data indicating an authenticated user and indicate to the smart contact lens 115 whether the user is authenticated.

At operation 415, when the user is authenticated, the smart contact lens 115 determines an object on which the user is focusing. The smart contact lens 115 determines the object on which the user is focusing, for example, using any combination of sensors such as the IR camera, an optical camera, a magnetic sensor, an accelerometer, a temperature sensor, a pressure sensor, and/or any other suitable sensor or measuring device. For example, the smart contact lens 115 determines the object on which the user is focusing based on a focal length determined according to data measured by the IR camera (e.g., size and/or shape of the user's eye) and a direction of focus according to a magnetic field detected by the magnetic sensor. In some examples, the determination of the object on which the user is focusing further includes one or more optical cameras viewing an environment from substantially the same vantage point as the user and the smart contact lens 115 and/or an accelerometer further specifying a direction of focus of the user.

At operation 420, the smart contact lens 115 determines one or more control inputs and/or control gestures. The control inputs and/or control gestures can take many forms, the scope of which is not limited herein. For example, the control inputs include at least one of movement of the user's head, movement of the user's eyes, and/or movement of the user's eyelids. In some examples, the control gestures further include movement of the user's body (e.g., movement of limbs such as movement of the user's foot or legs and/or movement of the user's fingers, hands, or arms).

At operation 425, a control signal is determined according to the object on which the user is focusing and the one or more control inputs and/or control gestures. In at least some examples, the control signal is determined according to a table associating objects that may be the subject of the user's focus, control inputs and/or control gestures, and control signals or desired actions. The table, in some examples, is the result of training, such as described above with respect to FIG. 3, and, in some examples, is refined on a continual or near-continual basis during use of the smart contact lens 115. In some examples, the smart contact lens 115 determines the control signal. In other examples, the smart contact lens 115 transmits data to the processing device 120 and the processing device 120 determines the control signal. In some examples, the processing device 120 further provides a signal to the smart contact lens 115 indicating the determined control signal.

At operation 430, the control signal determined at operation 425 is generated and transmitted to control one or more of the electronic devices 105A-105C. In some examples, a plurality of control signals are generated and transmitted (e.g., to control a scene involving more than one of the electronic devices 105A-105C and/or multiple operations by at least one of the electronic devices 105A-105C). In some examples, the smart contact lens 115 generates and/or transmits the control signal to control the one or more of the electronic devices 105A-105C. In other examples, the processing device 120 generates and/or transmits the control signal to control the one or more of the electronic devices 105A-105C. In yet other examples, the processing device 120 generates the control signal and provides the control signal to the smart contact lens 115 and the smart contact lens 115 subsequently transmits the control signal to control the one or more of the electronic devices 105A-105C.

In some examples, the method 400 further includes operation 435. At operation 435, the smart contact lens 115 determines user feedback including one or more control inputs and/or control gestures, a signal strength associated with one of the electronic devices 105A-105C to which the control signal was transmitted at operation 430, and one or more control inputs such as accelerometer output and magnetic sensor output. In at least some examples, the user feedback indicates an accuracy of the control signal according to an action or operation desired by the user. In some examples, the smart contact lens 115 utilizes the user feedback in a machine learning process to refine associations among objects that may be the subject of the user's focus, control inputs and/or control gestures, and control signals or desired actions. In other examples, the smart contact lens provides the data obtained at operation 435 to the processing device 120 for the processing device 120 to utilize in a machine learning process to refine associations among objects that may be the subject of the user's focus, control inputs and/or control gestures, and control signals or desired actions.

Figure 5:
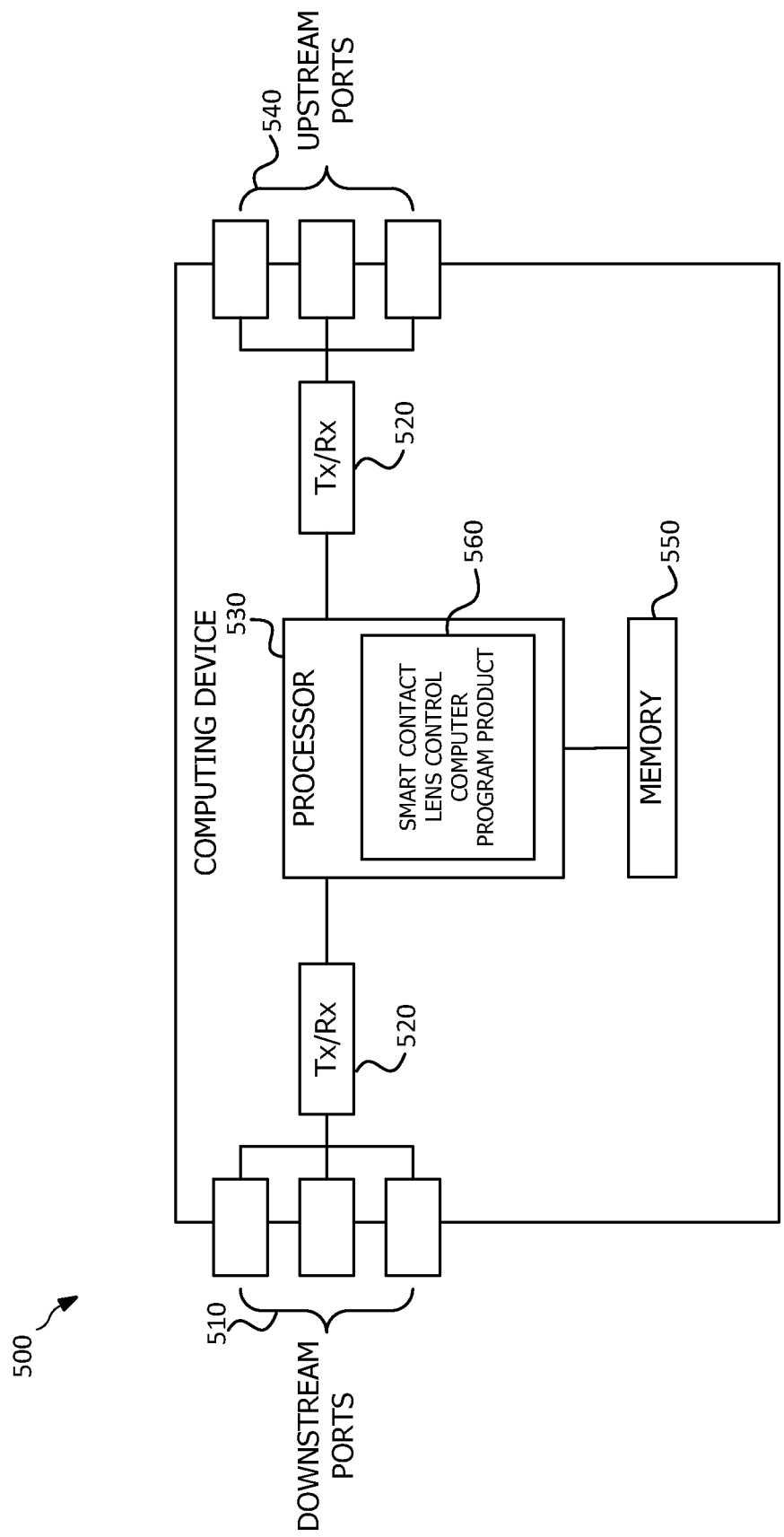
FIG. 5 depicts a computing device in accordance with various embodiments.

Referring now to FIG. 5, a schematic diagram of a computing device 500 according to various embodiments is shown. Computing device 500 is any suitable processing device capable of performing the functions disclosed herein such as smart contact lens, a processing device, a computer system, a server, a computing resource, a cloud-computing node, a cognitive computing system, etc. Computing device 500 is configured to implement at least some of the features/methods disclosed herein, for example, the smart contact lens control, such as described above with respect to system 100, smart contact lens 200, method 300, and/or method 400. For example, the computing device 500 is implemented as, or implements, any one or more of the smart contact lens 115 and/or the processing device 120. In various embodiments, for instance, the features/methods of this disclosure are implemented using hardware, firmware, and/or software (e.g., such as software modules) installed to run on hardware. In some embodiments, the software utilizes one or more software development kits (SDKs) or SDK functions to perform at least some of the features/methods of this disclosure.

Computing device 500 is a device (e.g., a smart contact lens, a processing device, a computer system, a server, a computing resource, a cloud-computing node, a cognitive computing system, a machine learning platform, etc.) that controls, or facilitates control of, one or more electronic devices based on a point of focus of a user and received control inputs and/or control gestures. In some examples, the computing device 500 is an all-in-one device that performs each of the aforementioned operations, or the computing device 500 is be a node that performs any one or more, or portion of one or more, of the aforementioned operations. In one embodiment, the computing device 500 is an apparatus and/or system configured to provide the smart contact lens control as described with respect to system 100, smart contact lens 200, method 300, and/or method 400, for example, according to a computer program product executed on, or by, at least one processor.

The computing device 500 comprises one or more input devices 510. Some of the input devices 510 include at least some of cameras, magnetic sensors, temperature sensors, pressure sensors, accelerometers, microphones, keyboards, touchscreens, buttons, toggle switches, and/or other devices that allow a user to interact with, and/or provide input actively or passively to, the computing device 500. Some other of the input devices 510 are downstream ports coupled to a transceiver (Tx/Rx) 520, which are transmitters, receivers, or combinations thereof. The Tx/Rx 520 transmits and/or receives data to and/or from other computing or electronic devices via at least some of the input devices 510. Similarly, the computing device 500 comprises a plurality of output devices 540. Some of the output devices 540 include at least some of speakers, a display screen (which, in some examples, is also an input device such as a touchscreen), lights, or any other device that allows a user to interact with, and receive output from, the computing device 500. At least some of the output devices 540 are upstream ports coupled to another Tx/Rx 520, wherein the Tx/Rx 520 transmits and/or receives data from other nodes via the upstream ports. The downstream ports and/or the upstream ports include electrical and/or optical transmitting and/or receiving components. In another embodiment, the computing device 500 comprises one or more antennas (not shown) coupled to the Tx/Rx 520. The Tx/Rx 520 transmits and/or receives data from other computing or storage devices wirelessly via the one or more antennas. In yet other embodiments, the computing device 500 includes additional Tx/Rx 520 such that the computing device 500 has multiple networking or communication interfaces, for example, such that the computing device 500 communicates with a first device using a first communication interface (e.g., such as via the Internet) and communicates with a second device using a second communication interface (e.g., such as another computing device 500 without using the Internet).

A processor 530 is coupled to the Tx/Rx 520 and at least some of the input devices 510 and/or output devices 540 and is configured to implement the smart contact lens control. In an embodiment, the processor 530 comprises one or more multi-core processors and/or memory modules 550, which functions as data stores, buffers, etc. The processor 530 is implemented as a general processor or as part of one or more application specific integrated circuits (ASICs), field-programmable gate arrays (FPGAs), and/or digital signal processors (DSPs). Although illustrated as a single processor, the processor 530 is not so limited and alternatively comprises multiple processors. The processor 530 further comprises processing logic configured to execute a smart contact lens control computer program product 560 that is configured to implement the smart contact lens control as described above with respect to system 100, smart contact lens 200, method 300, and/or method 400.

FIG. 5 also illustrates that a memory module 550 is coupled to the processor 530 and is a non-transitory medium configured to store various types of data. Memory module 550 comprises memory devices including secondary storage, read-only memory (ROM), and random access memory (RAM). The secondary storage is typically comprised of one or more disk drives, optical drives, solid-state drives (SSDs), and/or tape drives and is used for non-volatile storage of data and as an over-flow storage device if the RAM is not large enough to hold all working data. The secondary storage is used to store programs that are loaded into the RAM when such programs are selected for execution. The ROM is used to store instructions and perhaps data that are read during program execution. The ROM is a non-volatile memory device that typically has a small memory capacity relative to the larger memory capacity of the secondary storage. The RAM is used to store volatile data and perhaps to store instructions. Access to both the ROM and RAM is typically faster than to the secondary storage.

The memory module 550 houses the instructions for carrying out the various embodiments described herein. For example, the memory module 550 comprises the smart contact lens control computer program product 560, which is executed by processor 530.

It is understood that by programming and/or loading executable instructions onto the computing device 500, at least one of the processor 530 and/or the memory module 550 are changed, transforming the computing device 500 in part into a particular machine or apparatus, for example, a smart contact lens control system having the novel functionality taught by the present disclosure. It is fundamental to the electrical engineering and software engineering arts that functionality that can be implemented by loading executable software into a computer can be converted to a hardware implementation by well-known design rules known in the art. Decisions between implementing a concept in software versus hardware typically hinge on considerations of stability of the design and number of units to be produced rather than any issues involved in translating from the software domain to the hardware domain. Generally, a design that is still subject to frequent change is preferred to be implemented in software, because re-spinning a hardware implementation is more expensive than re-spinning a software design. Generally, a design that is stable and will be produced in large volume IS preferred to be implemented in hardware (e.g., in an ASIC) because for large production runs the hardware implementation IS less expensive than software implementations. Often a design IS developed and tested in a software form and then later transformed, by design rules well-known in the art, to an equivalent hardware implementation in an ASIC that hardwires the instructions of the software. In the same manner as a machine controlled by a new ASIC is a particular machine or apparatus, likewise a computer that has been programmed and/or loaded with executable instructions is a particular machine or apparatus.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a RAM, a ROM, an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, procedural programming languages, such as the "C" programming language, and functional programming languages such as Haskell or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider (ISP)). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Figure 6:
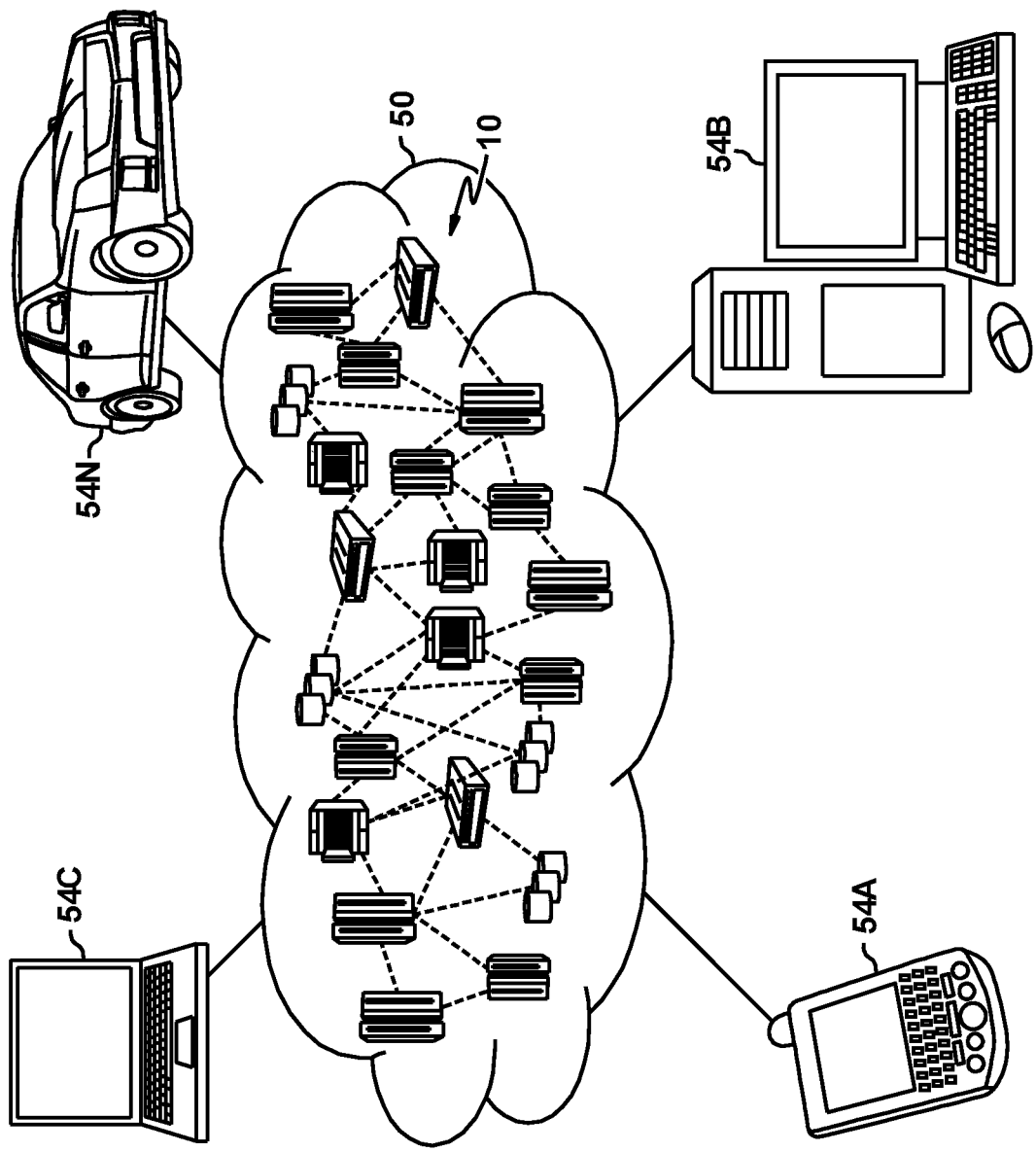
FIG. 6 depicts a cloud-computing environment according to various embodiments.
Figure 7:
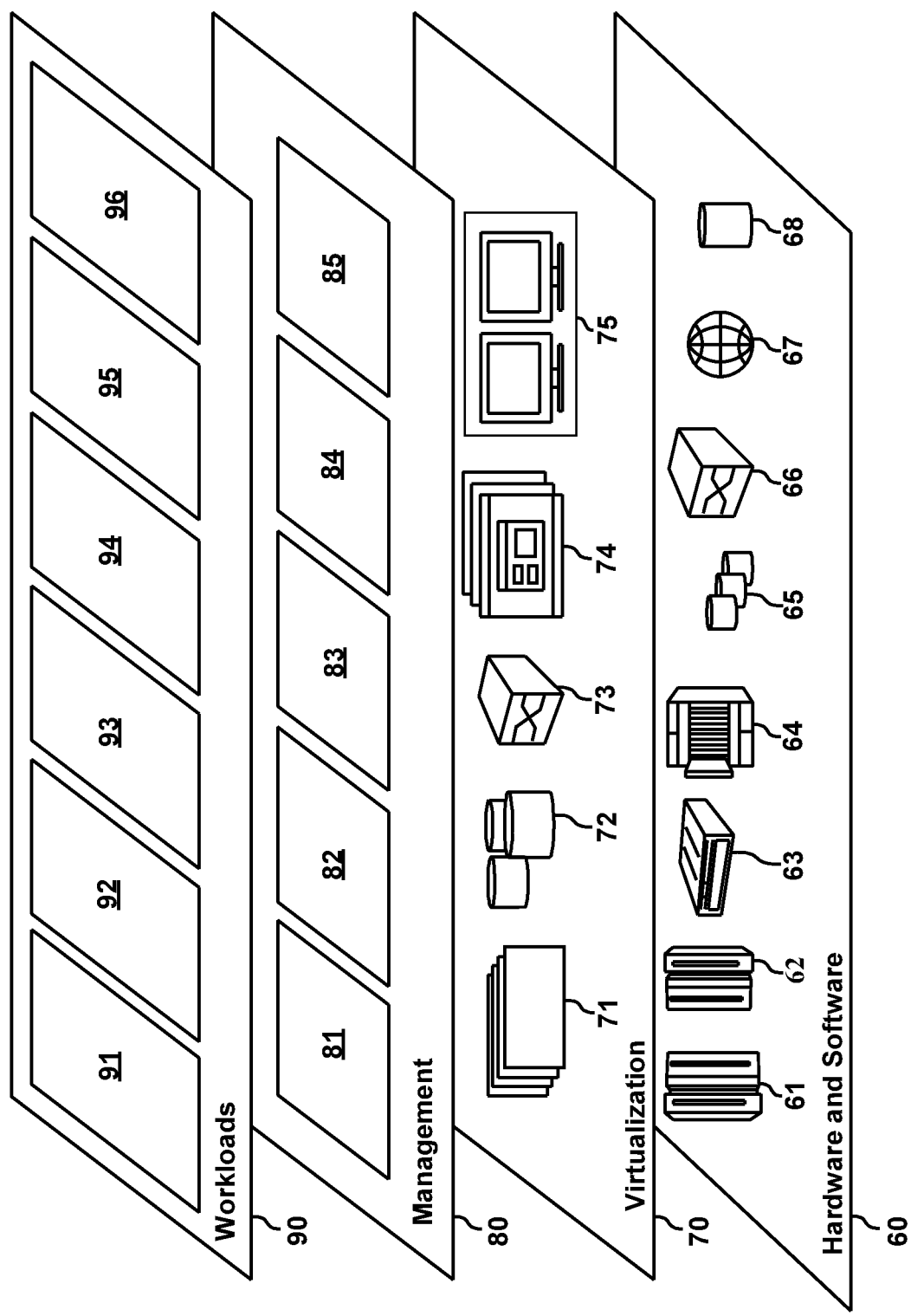
FIG. 7 depicts abstraction model layers according to various embodiments.

Turning now to FIG. 6 and FIG. 7, it is to be understood that although this disclosure includes a detailed description related to cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

The cloud model characteristics may include on-demand self-service, broad network access, resource pooling, rapid elasticity, and/or measured service. On-demand self-service is a characteristic in which a cloud consumer can unilaterally provision computing capabilities, such as server time and network storage, as needed automatically without requiring human interaction with the service's provider. Broad network access is a characteristic in which capabilities are available over a network and accessed through standard mechanisms that promote use by heterogeneous thin or thick client platforms (e.g., mobile phones, laptops, and personal digital assistants (PDAs)). Resource pooling is a characteristic in which the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter). Rapid elasticity is a characteristic in which capabilities can be rapidly and elastically provisioned, in some cases automatically, to quickly scale out and rapidly released to quickly scale in. To the consumer, the capabilities available for provisioning often appear to be unlimited and can be purchased in any quantity at any time. Measured service is a characteristic in which cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

The cloud model Service Models may include Software as a Service (SaaS), Platform as a Service (PaaS), and/or Infrastructure as a Service (IaaS).

SaaS is a service model in which the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings. PaaS is a service model in which the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations. IaaS is a service model in which the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

The cloud model Deployment Models may include private cloud, community cloud, public cloud, and/or hybrid cloud. Private cloud is a deployment model in which the cloud infrastructure is operated solely for an organization. It may be managed by the organization or a third party and may exist on-premises or off-premises. Community cloud is a deployment model in which the cloud infrastructure is shared by several organizations and supports a specific community that has shared concerns (e.g., mission, security requirements, policy, and compliance considerations). It may be managed by the organizations or a third party and may exist on-premises or off-premises. Public cloud is a deployment model in which the cloud infrastructure is made available to the general public or a large industry group and is owned by an organization selling cloud services. Hybrid cloud is a deployment model in which the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Referring now to FIG. 6, illustrative cloud computing environment 50 is depicted. As shown, cloud computing environment 50 includes one or more cloud computing nodes 10 with which local computing devices used by cloud consumers, such as, for example, PDA or cellular telephone 54A, desktop computer 54B, laptop computer 54C, and/or automobile computer system 54N may communicate. Cloud computing nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 6 are intended to be illustrative only and that cloud computing nodes 10 and cloud computing environment 50 can communicate with any type of computerized device over any type of network and/or network addressable connection (e.g., using a web browser).

Referring now to FIG. 7, a set of functional abstraction layers provided by cloud computing environment 50 (FIG. 6) is shown. It should be understood in advance that the components, layers, and functions shown in FIG. 9 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68. The hardware and software components of hardware and software layer 60 may serve as the underlying computing components on which cloud computing functions are executed in response to receipt of a request for performance of a function and/or service offered as a part of cloud computing environment 50 such as, for example, the smart contact lens control described above.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75. These virtual entities may enable a subscriber to cloud computing environment 50 to interact indirectly with the hardware and software components of hardware and software layer 60 indirectly via virtualization layer 70 without having a specific knowledge of, or interacting directly with, hardware and software layer 60. For example, a plurality of subscribers may interact with virtualization layer 70 to respectively access a corresponding plurality of virtual servers 71 and virtual storage 72 that all exist as separate threads, instances, partitions, etc. on a single server 62 and storage device 65, respectively. In such a scenario, virtualization layer 70 may cause each virtual server 71 and virtual storage 72 to appear to each subscriber as a dedicated and seamless computing and storage device, while enabling efficient operation of the hardware and software components of hardware and software layer 60 by reducing a potential for redundancy of components.

In one example, management layer 80 may provide the functions described below via an abstraction layer such that a subscriber to cloud computing environment 50 may interact with virtualization layer 70 and/or hardware and software layer 60 indirectly via management layer 80 without having a specific knowledge of, or interacting directly with, virtualization layer 70 and/or hardware and software layer 60. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provides pre-arrangement for, and procurement of, cloud computing resources for which a future requirement is anticipated in accordance with an SLA. Management layer 80 enables a subscriber to cloud computing environment 50 to interact with cloud computing environment 50 through management layer 80 to perform tasks and functions (e.g., administrative tasks) separate from actual execution of functions in the cloud computing environment 50. For example, an administrator may request access to a certain amount of computing resources (e.g., as provided in virtualization layer 70 and/or hardware and software layer 60) in cloud computing environment 50 via management layer 80 without having a specific knowledge of, or interacting directly with, virtualization layer 70 and/or hardware and software layer 60.

Workloads layer 90 provides examples of functionality for which the cloud computing environment may be utilized. The workloads and functions illustrated in workloads layer 90 are merely exemplary workloads and functions that may be executed in cloud computing environment 50 at the request or direction of a subscriber to cloud computing environment 50, and are not limited to those explicitly recited herein. Examples of workloads and functions which may be provided from this layer include: mapping and navigation 91; software development and lifecycle management 92; virtual classroom education delivery 93; data analytics processing 94; transaction processing 95; and smart contact lens control 96. These workloads and functions of workloads layer 90 may be end-user applications that enable a subscriber to cloud computing environment 50 to interact with any of management layer 80, virtualization layer 70, and/or hardware and software layer 60 indirectly via workloads layer 90 without having a specific knowledge of, or interacting directly with, any of management layer 80, virtualization layer 70, and/or hardware and software layer 60. In this manner, the subscriber and/or an end user who accesses cloud computing environment 50 may not require any form of specialized knowledge relating to the composition or operation of any of management layer 80, virtualization layer 70, and/or hardware and software layer 60 to perform the workloads and functions of workloads layer 90. In such a scenario, the workloads and functions of workloads layer 90 are said to be abstracted from management layer 80, virtualization layer 70, and hardware and software layer 60 because workloads layer 90 hides the underlying operation of management layer 80, virtualization layer 70, and hardware and software layer 60 from the subscriber and/or end-user while still enabling the subscriber and/or end-user to indirectly interact with management layer 80, virtualization layer 70, and/or hardware and software layer 60 to receive the computer processing benefits thereof via workloads layer 90.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

Certain terms are used throughout the following description and claims to refer to particular system components. As one skilled in the art will appreciate, different companies may refer to a component by different names. This document does not intend to distinguish between components that differ in name but not function. In the following discussion and in the claims, the terms "including" and "comprising" are used in an open-ended fashion, and thus should be interpreted to mean "including, but not limited to . . . ." Also, the term "couple" or "couples" is intended to mean either an indirect or direct wired or wireless connection. Thus, if a first device couples to a second device, that connection may be through a direct connection or through an indirect connection via other intervening devices and/or connections. Unless otherwise stated, "about," "approximately," or "substantially" preceding a value means +/−10 percent of the stated value or reference.

What is claimed is:

1. A computer program product comprising a computer readable storage medium having program instructions embodied therewith, the program instructions executable by a processor of a smart contact lens to cause the processor of the smart contact lens to:
   measure, by the smart contact lens, dimensions of a user's eye to determine a focal length of the user, the dimensions including a size and shape of the user's eye;
   measure, by the smart contact lens, a magnetic field proximate to the user's eye to determine a direction of focus of the user;
   receive, by the smart contact lens, a control input from the user;
   determine, by the smart contact lens, a control signal corresponding to the focal length of the user, the direction of focus of the user, and the received control input;
   generate, by the smart contact lens, the determined control signal; and
   control a first electronic device by transmitting, by the smart contact lens, the generated control signal to the first electronic device.

2. The computer program product of claim 1, wherein measuring the dimensions of the user's eye comprises capturing an infrared image of the user's eye via a back-side facing camera of the smart contact lens.

3. The computer program product of claim 2, wherein executing the instructions further causes the processor to authenticate the user for controlling the first electronic device by scanning a retina of the user via the back-side facing camera of the smart contact lens.

4. The computer program product of claim 1, wherein determining a direction of focus of the user further includes measuring a position and relative motion of a head of the user according to an accelerometer of the smart contact lens.

5. The computer program product of claim 1, wherein the control input comprises at least one of a movement of the user's eyes, a movement of a head of the user, movement of eyelids of the user, or movement of a portion of a body of the user.

6. The computer program product of claim 1, wherein executing the instructions further causes the processor to receive user feedback indicating an accuracy of an action performed by the first electronic device according to the generated control signal.

7. The computer program product of claim 1, wherein executing the instructions further causes the processor to:
determine, by the smart contact lens, a second control signal corresponding to the focal length of the user, the direction of focus of the user, and the received control input;
generate, by the smart contact lens, the determined second control signal; and
control a second electronic device by transmitting, by the smart contact lens, the generated second control signal to the second electronic device.

8. The computer program product of claim 1, wherein measuring the focal length of the user and the magnetic field proximate to the user's eye indicates an object on which the user is focusing.

9. The computer program product of claim 8, wherein the object on which the user is focusing is the first electronic device.

10. The computer program product of claim 8, wherein the object on which the user is focusing is an uncontrollable object that is not the first electronic device.

11. A computer-implemented method, comprising:
measuring, by a smart contact lens, dimensions of a user's eye to determine a focal length of the user, the dimensions including a size and shape of the user's eye;
measuring, by the smart contact lens, a magnetic field proximate to the user's eye to determine a direction of focus of the user;
receiving, by the smart contact lens, a control input from the user;
determining, by the smart contact lens, a control signal corresponding to the focal length of the user, the direction of focus of the user, and the received control input;
generating, by the smart contact lens, the determined control signal; and
controlling a first electronic device by transmitting, by the smart contact lens, the generated control signal to the first electronic device.

12. The computer-implemented method of claim 11, wherein measuring the dimensions of the user's eye comprises capturing an infrared image of the user's eye via a back-side facing camera of the smart contact lens, and wherein measuring the focal length of the user and the magnetic field proximate to the user's eye indicates an object on which the user is focusing.

13. The computer-implemented method of claim 12 wherein the object on which the user is focusing is the first electronic device.

14. The computer-implemented method of claim 12, wherein the object on which the user is focusing is an uncontrollable object that is not the first electronic device.

15. The computer-implemented method of claim 12, wherein the object on which the user is focusing is an object in a virtual environment.

16. The computer-implemented method of claim 11, further comprising
determining, by the smart contact lens, a second control signal corresponding to the focal length of the user, the direction of focus of the user, and the received control input;
generating, by the smart contact lens, the determined second control signal; and
controlling a second electronic device by transmitting, by the smart contact lens, the generated second control signal to the second electronic device.

17. A system, comprising:
a smart contact lens configured to:
determine an object on which a wearer of the smart contact lens is focusing based on a size and shape of an eye of the wearer;
determine a control input provided by the wearer of the smart contact lens;
generate a first control signal for controlling a first electronic device according to a result of a machine learning process including the determining of the object on which the wearer of the smart contact lens is focusing and the control input provided by the wearer of the smart contact lens; and
a processing device configured to:
receive a plurality of signals from the smart contact lens;
based on the received plurality of signals, determine an association between the object on which a wearer of the smart contact lens is focusing, the control input provided by the wearer of the smart contact lens, and the first control signal; and
provide the association between the object on which a wearer of the smart contact lens is focusing, the control input provided by the wearer of the smart contact lens, and the first control signal.

18. The system of claim 17, wherein determining the object on which the wearer of the smart contact lens is focusing comprises:
measuring dimensions of the eye of the wearer of the smart contact lens to determine a focal length of the wearer of the smart contact lens, the dimensions including the size and the shape of the eye of the wearer; and
measuring a magnetic field existing proximate to the eye of the wearer of the smart contact lens, and wherein determining the control input provided by the wearer of the smart contact lens.

19. The system of claim 17, wherein the processing device is further configured to:
receive feedback from the smart contact lens indicating an accuracy of an action corresponding to the control signal as compared to a desired action of the wearer of the smart contact lens; and
refine the result of a machine learning process according to the feedback received from the smart contact lens.

20. The system of claim 17, wherein the object on which a wearer of the smart contact lens is focusing is an object other than the first electronic device.

* * * * *